United States Patent [19]

Green et al.

[11] 4,304,866

[45] Dec. 8, 1981

[54] TRANSPLANTABLE SHEETS OF LIVING KERATINOUS TISSUE

[75] Inventors: Howard Green, Brookline; Olaniyi Kehinde, Mattapan, both of Mass.

[73] Assignee: Massachusetts Institute of Technology, Cambridge, Mass.

[21] Appl. No.: 94,003

[22] Filed: Nov. 14, 1979

[51] Int. Cl.$^3$ .............................................. C12N 5/00
[52] U.S. Cl. ...................................... 435/240; 424/95; 128/1 R; 128/305.5
[58] Field of Search ....................... 435/240, 241, 267; 424/95; 128/1, 305.5

[56] References Cited

U.S. PATENT DOCUMENTS 3,930,954  1/1976  Irie ................................. 435/241 X
4,016,036  4/1977  Green et al. ........................ 435/241

OTHER PUBLICATIONS

Eisinger et al., Chemical Abstracts, 92:3982g, (1980).

*Primary Examiner*—Esther M. Kepplinger
*Attorney, Agent, or Firm*—Arthur A. Smith, Jr.; David E. Brook

[57] ABSTRACT

A method of producing transplantable sheets of living keratinous tissue by culturing keratinocytes in a culture vessel and subsequently enzymatically detaching a sheet of keratinous tissue employing an enzyme, such as Dispase, is disclosed herein.

5 Claims, No Drawings

TRANSPLANTABLE SHEETS OF LIVING KERATINOUS TISSUE

DESCRIPTION

GOVERNMENT SUPPORT

The inventional described herein was made in the course of or under grants from the National Institutes of Health.

TECHNICAL FIELD

This invention is in the field of biology and more particularly in the field of cell biology.

BACKGROUND ART

Keratinocytes are a cell type which synthesize keratin and are able to form a stratified squamous epithelium. The most common keratinocytes are epidermal cells of the skin. Others include the cells lining the mouth, esophagus or vagina.

Although certain types of mammalian cells have been serially cultivated for many years, it has only been recently that techniques for the serial cultivation of keratinocytes, including human epidermal cells, have been developed. These recent techniques are described in Green et al., U.S. Pat. No. 4,016,036.

In the Green et al. patent, it is disclosed that human epidermal cells or other keratinocytes can be grown in cultures with fibroblast cells treated to prevent their multiplication. Fibroblast cell density is carefully controlled in these cultures to allow epidermal cell colony formation and growth. Keratinocytes also can be grown in the presence of fibroblast cell products as well as in the presence of fibroblast cells themselves. Using the Green et al. techniques disclosed in U.S. Pat. No. 4,016,036, it is possible to serially culture human epidermal cells and expand the number in the primary culture by many-fold.

In more recent work by Green, it has been discovered that agents known to increase the level of cellular cyclic-AMP can provide a dramatic effect on the growth of epithelial cells. Thus, agents such as cholera toxin, dibutyryl cyclic-AMP, methyl isobutyl xanthine and isoproterenol are employed to increase the multiplication of human epidermal cells in serial cultivation.

It is also known that disaggregated epidermal cells obtained directly from the epidermis or from briefly cultured cells can be applied to a graft bed and reconstitute an epidermis. See Billingham, R. E. and Reynolds, J., *Brit. J. Plastic Surg.*, 5:25–36 (1952); and Yuspa, S. H., Morgan, D. L., Walker, R. J. and Bates, R. R. *J. Invest. Dermatol.*, 55:379–389 (1970). Nevertheless, use of the disaggregated epidermal cells is probably not the most efficient method of grafting cultured cells. Since the stratification in cell cultures is such that the multiplying cells lie on the surface of the dish, it would be desirable to retain this polarity in the graft by applying an intact culture-grown epithelium, rather than disaggregated cells, of which a large fraction would be incapable of multiplication.

A method for employing a culture epithelium has been disclosed in which cultures are grown on transplantable collagen surfaces. See Worst, P. K. M., Valentine, E. A. and Fusenig, N. E., *J. Natl. Cancer Institute*, 53:1061–1064 (1974). Although it would be highly desirable, there has not heretofore been a method for detaching confluent epidermal sheets from the surface of a petri dish without disassociating the cells.

DISCLOSURE OF THE INVENTION

This invention relates to a novel and unique method of producing transplantable sheets of living keratinous tissue, including epidermal cell tissue. In this method, keratinocytes are cultured in a culture dish under conditions whereby a sheet of keratinous tissue is formed upon the surface of the culture dish. The keratinous tissue is then detached from the surface of the culture dish without disaggregating the individual cells. In a preferred embodiment, the sheet of keratinous tissue is detached from the surface of the culture dish by treating the tissue with the neutral protease Dispase.

This method allows large amounts of living keratinous tissue, such as that formed from epidermal cells, to be grown in culture starting with epidermal cells from a donor having a denuded epithelial area needing treatment. Large amounts of tissue can be grown quickly in culture dishes and then detached in sheet form for transplantation directly onto the injured donor.

Detached sheets of keratinous tissue can also be used in the screening of drugs for their dermatological properties.

BEST MODE OF CARRYING OUT THE INVENTION

This invention relates to the serial cultivation of keratinocytes, including human epidermal cells. Because of this, many of the teachings of U.S. Pat. No. 4,016,036 and copending application Ser. No. 961,444, apply to this invention. In view of this, the teachings of both the issued patent and pending application are hereby incorporated by reference.

By employing the techniques described in U.S. Pat. No. 4,016,036 and pending application Ser. No. 961,444, it has been found that large scale cultivation of epithelial cells obtained from a donor is practical. For example, starting with 1 $cm^2$ of newborn skin, and employing an inoculation density of $10^4$ cells, the area of culture epithelium can be expanded to 0.6 square meters in 14–21 days. The increase in area is about 6000—fold. Since the epithelium shrinks after its detachment from the surface of a culture dish to about 1/4th its area while attached, the overall expansion of epithelium typically might be 1,500-fold. The growth may also be evaluated from the number of cells produced; since each confluent 50 mm primary culture contains about $5 \times 10^6$ cells, the overall increase of cell number would be about 500-fold.

The possible yield of epithelium from a secondary subculture may also be estimated from the following example: If 30 primary cultures were initiated with $10^5$ cells each, and allowed to grow to $10^6$ cells each, the yield would be $3 \times 10^7$; this requires about 12 days. The cultures would be subconfluent, still growing fairly rapidly, and able to form colonies on transfer with high efficiency. $2 \times 10^4$ cells could then be transferred into each of 1500 cultures. These cultures should be confluent in about 10–12 days, yielding 3 square meters of epithelium. Of course, the inoculation density, the time allowed and the yield can be varied according to requirement.

Despite the success in serially cultivating epithelial cells to a point where sheets of stratified squamous epithelium existed, it was very difficult to remove these sheets from the culture dish without destroying them.

Attempts to scrape the sheets off of the dish resulted in shredding of the epithelium. Treatment with trypsin alone, trypsin with scraping, collagenase, and ethylene diamine tetraacetic acid (EDTA) also failed to produce sheet detachment without concomitant damage.

Although most techniques to separate sheets of keratinous tissue failed, it was found that one enzyme, a neutral protease sold under the trade name Dispase, separated the sheets without disaggregating or disassociating the cells. Commercially, Dispase is available from Boehringer-Mannheim.

The neutral protease Dispase is described in U.S. Pat. No. 3,930,954 issued to Irie. Therein, it is stated that this enzyme is produced by a strain of Bacillus polymyxa deposited at American Type Culture Collection under accession number ATCC 21993 (and also deposited at the Japanese Fermentation Research Institute Agency of Industry and Technology under accession number FERM-P-No. 412).

The protease is produced by carrying out a liquid culture for 2 to 7 days at pH 5 to 8 under a temperature of 20° to 37° C. on a synthetic medium or a natural medium containing a suitable amount of carbohydrate, a nitrogen source and inorganic salts respectively. Any method of surface culture, shaken culture or culture under aeration can be employed, but shaken culture and culture under aeration are generally preferred.

After the completion of the culture, the bacterial cells are removed and the protease solution is obtained. The thus obtained protease solution is subjected to a purification operation such as salting out, precipitation by solvent, concentration under reduced pressure and the like to obtain a concentrated protease solution. Most of the active protease is precipitated by salting out the concentrated protease solution with 60 to 80% saturated ammonium sulfate solution. The precipitation can also be carried out with 75% methanol, 70% ethanol, 60% acetone or 70% isopropanol, the yield of the active protease being 88%, 80%, 70% and 75%, respectively. The crude protease thus obtained can be preserved in quite a stable state at pH 4–9 under a temperature of 5° C. for 7 days, and it can be similarly preserved at 27° C. for 24 hours.

The protease obtained has the following chemical and physical properties:

a. Function: The protease functions as a neutral protease.

b. Specificity to substrate: This protease has a mild proteolytic activity to casein.

c. Optimum pH value and stable pH range: Optimum pH: The optimum pH for proteolytic activity to casein is 8.5. Stable pH range: This protease is very stable within the pH range of 4.0 to 9.0.

d. Assay method of activity: The activity is expressed in units of hemoglobin in accordance with Anson's Method.

e. Active temperature range: This protease is active within the temperature range of 20° to 75° C. The optimum temperature is 60° C.

f. Inactivation by pH and temperature: The activity is completely lost at a pH of below 3.0 and at a pH of above 10.0. The activity is also completely lost by heating at 65° C. for 10 minutes.

g. Inhibition and activation: The activity is inhibited by metal-chelating agents such as ethylenediaminetetraacetate (EDTA), citric acid, o-phenanthroline, 2,2′-dipyridyl and sodium fluoride, and oxidizing agents such as N-bromosuccinimide (NBS) and iodine. The activity is enhanced by the addition of metallic ions such as $Ca^{++}$, $Mn^{++}$, $Mg^{++}$, $Fe^{++}$, $Fe^{+++}$ and $Al^{+++}$.

h. Method of purification: The crude protease is crystallized by the following procedure. The crude protease is dissolved in M/500 calcium acetate solution, and the insoluble material is removed by filtration or centrifuge. Ammonium sulfate is added to the filtrate to make a 40% saturated solution, and the precipitated material (nonactive fraction) is removed by filtration or centrifuging. Further ammonium sulfate is added to the resultant filtrate to make a 70% saturated solution, and the precipitated material is recovered by filtration or centrifuging. The precipitated material thus obtained (which is precipitated from 70% saturated ammonium sulfate solution) is dissolved in M/500 calcium acetate solution, and the resultant solution is subjected to dialysis in a cellophane tube or bladder membrane against M/500 calcium acetate solution. The cellophane tube or bladder membrane permits passage of ammonium sulfate but not the protease. The dialysis is carried out at 5° C., and after 3 days the inside solution in the semipermeable membrane begins to crystallize. After 7 days, the crystallized material is recovered by centrifuging. The crystallized material thus obtained is mixed with M/500 calcium acetate solution to form a suspension, and is dissolved by adding dilute NaOH solution dropwise at a low temperature. Immediately after the addition of the NaOH solution, dilute HCl solution is added to make the pH value of the solution 8.0, and the insoluble material is removed by centrifuging. The pH value of the solution is then made 6.8. The resultant solution is allowed to stand at a low temperature to crystallize out the protease.

i. Molecular weight: In accordance with ultracentrifugal analysis, the molecular weight of the protease was determined to be 35,900.

j. Crystal structure: The crystal structure of the protease has not been fully determined, but the crystal obtained in accordance with the purification method of Item (h) was stick-like or needle-like.

k. Elemental analysis: The elemental analysis of the crystal obtained in accordance with the purification method of Item (h) was as follows: C: 46.57%, H: 7.17%, O: 31.57%, N: 14.48%, and S: 0.21%.

The protease was found to attack peptide bonds in the "oxidized B-chain" of insulin at the following twelve positions: Phe(1)-Val(2), His(5)-Leu(6), His(10)-Leu(11), Glu(13)-Ala(14), Ala(14)-Leu(15), Leu(15)-Tyr(16), Tyr(16)-Leu(17), Leu(17)-Val(18), Gly(23)-Phe(24), Phe(24)-Phe(25), Phe(25)-Tyr(26) and Lys(29)-Ala(30).

Additional information about this neutral protease can be found in U.S. Pat. No. 3,930,954 and in the following articles, the teachings of which are hereby incorporated by reference: Matsumura, T., Yamanaka, T., Hashizume, S., Irie, Y. and Nitta, K., *Japan. J. Exp. Med.*, 45:377–382 (1975); and Matsumura, T., Nitta, K., Yoshikawa, M., Takaoka, T. and Katsuta, H., *Japan. J. Exp. Med.*, 45:383–392 (1975).

Studies indicated that epidermal cells contained in sheets of tissue grown in culture and separated with Dispase remained perfectly viable after separation.

This invention can be more specifically illustrated by the following examples.

EXAMPLE 1

Formation of Primary Culture Epithelium

Employing the procedures of Example 9 in U.S. Pat. No. 4,016,036, primary cultures of epidermal cells derived from the skin of donors of various ages were formed. Foreskin of newborns was employed and cells from older donors were derived from skin over the knee or thigh, removed in the course of scar revision for orthopedic surgery on patients with chronic arthritis. 50 mm tissue culture petri dishes were inoculated with $10^3$, $10^4$ and $10^5$ trypsin-disaggregaged cells, together with or following $4 \times 10^5$ lethally irradiated 3T3 cells, and cultivated. The cultures each contained cholera toxin at $10^{-10}$ M beginning at the time of inoculation, and EGF at 10 μg/ml beginning 3-5 days later. Keratinocyte colonies appeared within a few days, and as they expanded, displaced the 3T3 cells from the surface. The time required for the colonies to become confluent in cultures inoculated with $10^4$ or $10^5$ cells is shown in Table 1. The colony-forming efficiency was derived from the cultures inoculated with $10^3$ cells; these cultures were fixed and stained with Rhodanile blue when the colonies were still discrete.

TABLE 1

| Strain | Age of Donor | Time Elapsed before cultivation | Plating Efficiency (%) | Time for $10^4$ cells to reach confluence | Time for $10^5$ cells to reach confluence |
| --- | --- | --- | --- | --- | --- |
| AA | newborn | 2 hrs | — | — | 15 days |
| AB | newborn | 4 hrs | 3.4 | 14 days | 11 days |
| AC | newborn | 3½ hrs | 4.4 | 19 days | 15 days |
| AK | newborn | 1½ hrs | 2.1 | — | 14 days |
| AE | 45 yr. | 18 hrs | 1.5 | — | 15 days |
| AI | 49 yr. | 2 hrs | 0.9 | 21 days | 17 days |
| AD | 70 yr. | 48 hrs | — | — | 19 days |
| AJ | 84 yr. | 5 hrs | 0.6 | — | 20 days |

It can be seen from Table 1 that most cultures inoculated with $10^5$ cells reached confluence in 14-17 days. Culture inoculated with $10^4$ cells required an additional four days to become confluent. The colony-forming efficiency ranged from slightly less than 1% for older donors to as high as 4% for newborns.

The colony-forming efficiency is an average for all cells obtained from the trypsinized skin. These values do not tell the colony-forming efficiency of the multiplying subpopulation of the epidermis—the basal cells. Though the skin was trimmed of excess subcutaneous tissue before enzymatic disaggregation, half the cells obtained could easily have been connective tissue cells. Of the epidermal cells, probably more than half were terminally differentiated and unable to start colonies. The colony-forming efficiency of the basal cells in the skin might easily have been more than four-fold higher than the overall values listed in Table 1.

EXAMPLE 2

Plating Efficiency of Human Epidermal Cells of Expanding (Subconfluent) Cultures The colony-forming efficiency of the cells of subconfluent primary and secondary cultures was studied. Most strains were those described in Example 1. An additional strain, CS-1, orginated from the abdominal skin taken for revision of a scar during Caesarian Section. Part of the original biopsy preserved frozen for several years was thawed and grown as described in Example 1. A clone was isolated from the primary culture, expanded in secondary culture and its plating efficiency measured in tertiary culture.

The results are presented in Table 2 below.

TABLE 2

| | | Plating Efficiency (%) of Cells Taken From | |
| --- | --- | --- | --- |
| Age of Donor | Strain | Primary Culture | Secondary Culture |
| Newborn | AB | 28.5 | — |
| Newborn | AK | 11.7 | — |
| 34 | CS-1 | — | 16.9 (clone) |
| 49 | AI | 6.7 | — |
| 70 | AD | 28 | 23 |
| 84 | AJ | 9.6 | — |

As can be seen, the colony-forming efficiency of the cells of subconfluent primary and secondary cultures was much higher than that of the primary cells when they were trypsinized and transferred. Whether derived from old or young donors, these cells formed new colonies with an efficiency of from 6 to nearly 30%. Any effect of donor age was not evident.

Certain of the confluent epithelia grown in Example 1 were treated with Dispase II (the less purified form) at 1.2 μg/ml in serum-free medium, the volume being sufficient to permit acess of the enzyme to the free edge of the epithelium, which, two weeks after inoculation, extended part way up the side wall of the petri dish. After about 30 minutes at 37°, the process of detachment began at the free edge, and moving downward and then centrally was usually complete in about 1 hour. The epithelium separated from the plastic surface as a disc with a slightly curled edge derived from the cells that had grown on the wall of the dish. The epithelium was very elastic and contracted to as little as 2 cm in diameter, becoming thicker in the process and acquiring a puckered appearance under the low power microscope. Very few epidermal cells detached from the epithelium, and none were left on the dish surface; but if any human fibroblasts were present, some could be detected after detachment on the epithelium because they remained attached to the surface of the dish. The detached epithelium could be picked up with a forceps and transferred to another vessel, and its polarity could be determined at any time by the orientation of the curled edge.

EXAMPLE 4

Viability of Epidermal Cells in Detached Tissue

In order to determine the viability of epidermal cells in detached epithelia of Example 3, the detached sheets were washed free of Dispase and disaggregated with trypsin and EDTA. The colony-forming efficiency of the cells was then compared with that of the cells of a duplicate epithelium disaggregated directly with trypsin and EDTA. The results are presented in Table 3.

TABLE 3

| Cell Strain | Inoculum Size | Serial Transfer of Cells Forming the Epithelium Tested | Time at Confluence (days) | Subsequent Colony Forming Efficiency (%) | |
|---|---|---|---|---|---|
| | | | | Detached with Dispase Then Disaggregated | Disaggregated Directly |
| AN* | $10^5$ | Primary | 1 | 15 | 23 |
| AN* | $10^5$ | Primary | 4 | 23 | 18 |
| AO* | $10^5$ | Primary | 1 | 30 | 33 |
| AQ* | $10^5$ | Primary | 2 | 27 | 25 |
| AB | $10^4$ | Tertiary | 5 | 11 | 13 |
| AD | $10^4$ | Secondary | 1 | 4.0 | 5.1 |
| AD | $10^4$ | Secondary | 4 | 4.3 | 1.9 |
| AJ | $10^4$ | Secondary | 1 | 0.8 | 0.9 |
| AJ | $10^4$ | Secondary | 3 | 0.8 | 0.4 |

*Derived from skin of newborns

Table 3 shows that the Dipase treatment had virtually no effect on the viability of the epidermal cells. The epidermal cells of newborns preserved high colony-forming efficiency even after several days in the confluent state, while those of elderly donors (AD and AJ) declined very sharply in comparison with their behavior in expanding cultures. This probably indicates that the cells of the elderly donors have a much higher tendency to differentiate terminally in confluent culture.

EXAMPLE 5

Comparative Epithelium Detachment Techniques

Other techniques were employed in efforts to detach epithelium grown in petri dishes according to Example 1. These all failed, and a summary of the procedures and results is presented in Table 4 as follows:

TABLE 4

| Treatment | Results |
|---|---|
| Remove growth medium; scrape gently with rubber spatula beginning at edges of dish | Shredding of epithelium |
| Incubate with trypsin alone (0.1% and 0.25%) | Cell layer splits Detachment of cell clumps from superficial part only |
| Trypsin (0.25%) and scraping | Shredding of epithelium |
| EDTA (0.02%) and scraping | Epithelium detached, sometimes shredded. Cells of detached epithelium non-viable when reinoculated |
| Collagenase (0.25%) | No detachment |

EXAMPLE 6

In Vivo Skin Grafts

Human skin was obtained either from the foreskin of newborns or from the knee or thigh of adults. Following removal of the subcutaneous tissue and as much dermis as possible, the tissue was minced and trypsinized and $10^5$ cells were plated onto 50 mm Flacon tissue culture dishes containing $4 \times 10^5$ lethally irradiated 3T3 cells. The cultures were fed with fortified Eagle's medium supplemented with 20% fetal calf serum, $10^{-10}$ M cholera toxin and 0.4 µg/ml hydrocortisone. The cultures were incubated at 37° C. in a 10% $CO_2$ atmosphere. Beginning 2–3 days after inoculation, epidermal growth factor (10 ng/ml) was also added to the culture medium. The medium was changed every 3 to 4 days until the cultures became confluent (11–25 days).

Cultured epithelium was detached intact from the surface of the tissue culture dish using the enzyme Dispase. Cultures of confluent epithelium were washed twice with serum-free medium, and 8 ml of this medium containing 5 mg/ml (1–2 µ/ml) of Dispase II (Boehringer-Mannheim, Indianapolis, Inc.) were added. Within 45 minutes to 1 hour at 37° C., the epithelium detached as an intact sheet, which then shrank to a diameter of about 2 cm. The enzyme solution was carefully aspirated and the epithelium was washed twice with medium containing 20% fetal calf serum.

Vaseline-impregnated gauze was cut into 2 cm circles using sterile conditions. A circular gauze was then transferred by means of forceps to the surface of the cultured epithelium. While holding the gauze and cell sheet gently at one point with forceps, the surface of the gauze was stroked lightly with a rubber policeman in order to attach the epithelium to the gauze. Then the gauze and attached epithelium were turned over in the dish so that the epithelium was now on top, the basal cell layer being the most superficial. The epithelium was then gently but evenly spread over the underlying gauze with a forceps and the edges of the epithelium were tucked under the gauze to anchor it. 2.0 ml of medium containing 20% fetal calf serum were added to the epithelium and dish. This preparation was then placed in an atmosphere containing 10% $CO_2$ in a glass jar and transported to the surgery room.

The grafting techniques were as follows. 0.1 ml/10 gms of body weight of a sterile 3.6% solution of chloral hydrate dissolved in isotonic phosphate buffer was used to anesthetize 4–6 week old congenitally athymic "nude" mice (Balb-C, Sprague Dawley). A rectangular graft bed, approximately 2 cm by 2 cm, was prepared on the dorso-lateral side just over the rib cage. Full thickness skin down to the panniculus carnosus was removed using curved scissors. The scissors and graft bed were kept moistened with isotonic buffer. The vaseline-impregnated gauze bearing the cultured epithelium was trimmed if necessary and inverted on the graft bed so that the basal layer of the epithelium was in contact with the bed and the terminally differentiating cells were superficial and covered by the gauze. A larger piece of vaseline gauze was then applied, and the graft was held firmly by a single Band-Aid Strip (Johnson and Johnson, New Brunswick, New Jersey). Several turns of adhesive tape (Zonas Tape, Johnson and Johnson) were then applied to further secure the bandage against the efforts of the mouse to remove it. Six days later the bandage was cut with scissors and removed gently with forceps. After inspection of the graft, the site was rebandaged, usually with the aid of light ether anesthesia. The initial success of the grafts (primary take) was evaluated from their appearance and their attachment to underlying tissue. A strobe camera was used to record changes in gross appearance of the grafts with time. Control experiments were also conducted to follow the covering of an ungrafted bed by migration and proliferation of adjacent mouse epidermal cells.

Grafts to be examined histologically were surgically removed together with the surrounding mouse skin and often the underlying musculature. The tissue was fixed in 3.7% formaldehyde, dehydrated and embedded in paraffin. Paraffin was removed from serial sections with xylene and the sections were rehydrated. One section was stained with hematoxyline and eosin, and a consecutive section was strained by immunofluorescence using rabbit antiserum against a purified precursor protein of the human cross-linked envelope. Briefly, the section was treated with 40 $\mu$l of a 1/20 dilution of the rabbit antiserum in isotonic phosphate buffer and incubated for 30 minutes at 37° C. The section was then carried through 3 successive 5 minute washes with the buffer. 40 $\mu$l of a 1/16 dilution of fluorescein-conjugated goat anti-rabbit globulin (Miles Laboratories) was added to the section and incubated for 30 minutes at 37° C. Following 3 successive 5 minute washes, a glass coverslip was mounted over the section using gelvatol. Photographs were taken with a Universal Zeiss Microscope using Tri-X film and developed with diafine developer.

Table 5 illustrates data for over 100 grafts. Nearly all showed a primary take except where infection had occurred. At this stage the grafts were very fragile. In control animals in which a graft bed was made but no graft applied, a complete epidermis was formed over the graft bed by migrated mouse epidermal cells within 9-10 days. The appearance of this epithelium could not be distinguished from that of grafted human epithelium. Whether grafted or not, the wound contracted progressively, chiefly in the anterio-posterior axis. In animals grafted with human epithelium, contraction was inhibited somewhat, but generally the final size of the wound was about 1.5 cm×0.3 cm.

species-specific, and an antiserum prepared against the human precursor protein can be used to distinguish human from mouse keratinocytes.

As demonstrated earlier on frozen sections, the antiserum stains approximately the outer half of the human epidermis, including the outer spinous cell layer, the granular layer and the stratum corneum. When examined in sections of formaline fixed tissue, the spinous and granular layers stained well but the stratum corneum did not, probably because the formalin fixation prevented penetration of the antiserum. The antiserum did not stain any part of mouse epidermis.

The grafts and surrounding mouse skin was then excised at different times, and consecutive sections were stained either with hematoxylin and eosin or with the antiserum. The appearance of an entire graft maintained on a mouse for 108 days showed that the epidermis surrounding the original wound (in situ epidermis) was revealed at both ends of the tissue by the presence of underlying hair follicles and sebaceous glands. The mouse epidermal cells that migrated over the wound reconstituted epidermis of about the same thickness but did not form hair follicles or sebaceous glands in the underlying dermis. Neither type of mouse epidermis was stained by immunofluorescence. The human epidermis, located by the fluorescence, occupied about 2/3 of the length of the (contracted) graft bed. The epidermis was more stratified, and thicker than mouse epidermis, and possessed a well-defined granular layer and stratum corneum. It resembled in most respects normal human epidermis but, as was true for the migrated mouse epidermis, there were no hair follicles or sebaceous glands.

Out of 21 grafts examined immunologically 6-108 days after grafting, 14 possessed human epidermis.

The culture-grown epithelium prior to its detachment consisted of a very flattened basal layer of mitotically active cells and numerous upper layers of larger and also flattened differentiating cells. The cultured epithe-

TABLE 5

Transplantation of Cultured Human Epithelium Onto Congenitally Athymic Mice

| Strain | Age of Donor | Transfer History of Cells Forming the Culture Epithelium used for Grafting | No. of Cells Inoculated per dish | Time at Confluence (days) | No.* Mice Grafted | #Duration of Graft at time of Immunological Testing (days) |
|---|---|---|---|---|---|---|
| AN | Newborn | Primary | $10^6$ | 7 | 2 | 108 |
| AN | Newborn | Primary | $10^4$ | 6 | 5 | 89 |
| AN | Newborn | Secondary | $10^4$ | 3 | 1 | — |
| AO | Newborn | Primary | $10^5$ | 4 or 9 | 5 | 10 |
| AO | Newborn | Secondary | $10^5$ | 1 | 6 | 58 |
| NK5 | Newborn | 5th transfer (clone) | $10^5$ | 2 | 16 | — |
| NK6 | Newborn | 6th transfer (clone) | $10^5$ | 2 | 6 | — |
| RoCi | 12 yrs | Primary | $10^4, 10^5$ or $3 \times 10^5$ | 7 or 14 | 24 | 9,30,32,[50],[54],[70] |
| AD | 70 yrs | Secondary | $2 \times 10^4$ | 2 or 4 | 3 | 17 |
| AD | 70 yrs | Tertiary | $5 \times 10^4$ | 1 or 2 | 14 | 10,25,[48],[61] |
| AJ | 84 yrs | Secondary | $2 \times 10^5$ | 1,4,5 or 16 | 5 | — |
| AJ | 84 yrs | Tertiary | $5 \times 10^4$ | 0 or 1 | 14 | 11,33,[50],[78] |
| FrBa | 38 yrs | Primary | $10^5$ | 5 | 10 | 6,20 |

*Nearly all grafts showed primary take at 6 days
Unbracketed numbers - human epidermis present; bracketed numbers - human epidermis absent.

Because of the remarkable ability of the mouse epidermal cells to cover the wound by growing in from its margins, it became necessary to find a method of distinguishing between human and mouse epidermis. Epidermal cells synthesize a protein that moves to the cytoplasmic surface of the plasma membrane and late in terminal differentiation becomes cross-linked enzymatically to form an insoluble envelope. Although the epidermal keratins of the mouse and the human cross-react immunologically, the envelope precursor protein is lium did not possess a well-defined granular layer or stratum corneum. Within 10 days after the cultured epithelium was grafted onto a nude mouse, it resembled normal human epidermis in most respects. It consisted of a stratified squamous epithelium composed of 5 to 8 cell layers with a prominent granular layer and a well-defined stratum corneum. The cell layers were somewhat flattened in comparison with those of normal epidermis and the epidermal-dermal junction lacked rete pegs. Over succeeding weeks the architecture of the grafted epithelium became more typical of epidermis. At 108 days after grafting, the basal cells had assumed a normal orientation perpendicular to the basement membrane, the outer spinous cells were larger and less flattened, and numerous rete pegs were present.

Grafts prepared in a similar manner as described above were applied to a male burn victim, and also took in a similar manner.

Industrial Applicability

This invention is useful in the serial cultivation of keratinocytes to produce transplantable living keratinous tissue, including tissue of human epidermal cells. Such tissue can be used in the treatment of denuded areas of humans or other mammals, or the tissue can be used in the screening of drugs for their dermatological properties.

Equivalents

Those skilled in the art will also recognize, or be able to determine using no more than routine experimentation, other equivalents to the specific embodiments described herein. For example, although the term "culture dish" has been used to describe the vessel in which keratinocytes are cultured, any other vessel suitable fo culturing keratinocytes is suitable. Such equivalents are intended to be covered by the claims appended hereto.

We claim:

1. A method of producing transplantable sheets of living keratinous tissue, comprising:
    a. culturing keratinocytes in a culture vessel under conditions whereby a sheet of keratinous tissue is formed upon the surface of the vessel, and
    b. incubating said sheet of keratinous tissue in the presence of a neutral protease under conditions sufficient to enzymatically detach the sheet of keratinous tissue from the surface of the vessel without disaggregating said sheet.

2. A method of claim 1 wherein the keratinocytes comprise human epidermal cells.

3. A method of claim 2 wherein the culturing of keratinocytes is performed in the presence of fibroblast cells treated to prevent their multiplication or medium sufficiently conditioned by fibroblast cells to allow keratinocyte colonies to grow.

4. A method for treating defects in the epithelium of a mammal, comprising:
    a. obtaining living epidermal cells from said mammal;
    b. culturing said epidermal cells in a culture vessel to form a sheet of epidermal tissue in said vessel;
    c. incubating said sheet of epidermal tissue in the presence of a neutral protease under conditions sufficient to enzymatically detach said tissue from the culture vessel without disaggregating the epidermal cells; and,
    d. transplanting detached epidermal tissue onto the defect of said mammal.

5. A method of claim 4 wherein the mammal comprises a human being.

* * * * *